(12) United States Patent
Rudo

(10) Patent No.: US 7,186,760 B2
(45) Date of Patent: Mar. 6, 2007

(54) TRIAXIAL WEAVE FOR REINFORCING DENTAL RESINS

(75) Inventor: David N. Rudo, Seattle, WA (US)

(73) Assignee: Ribbond, Inc., Seattle, WA (US)

( * ) Notice: Subject to any disclaimer, the term of this patent is extended or adjusted under 35 U.S.C. 154(b) by 159 days.

(21) Appl. No.: 10/656,088

(22) Filed: Sep. 5, 2003

(65) Prior Publication Data

US 2004/0048949 A1    Mar. 11, 2004

Related U.S. Application Data

(63) Continuation of application No. 09/807,560, filed as application No. PCT/US99/23563 on Oct. 8, 1999, now abandoned.

(60) Provisional application No. 60/104,265, filed on Oct. 14, 1998.

(51) Int. Cl.
*A61K 6/08* (2006.01)
*A61C 3/00* (2006.01)

(52) U.S. Cl. ............... 523/115; 523/116; 523/118; 523/222; 433/228.1

(58) Field of Classification Search ........... 523/115, 523/116, 118, 222; 433/228.1
See application file for complete search history.

(56) References Cited

U.S. PATENT DOCUMENTS

| | | | |
|---|---|---|---|
| 4,610,688 A | 9/1986 | Silvestrini et al. | |
| 4,816,028 A | 3/1989 | Kapadia et al. | |
| 4,960,349 A * | 10/1990 | Willibey et al. | ............ 405/262 |
| 5,098,304 A | 3/1992 | Scharf | |
| 5,176,951 A | 1/1993 | Rudo | |
| 5,314,492 A | 5/1994 | Hamilton et al. | |
| 5,921,778 A | 7/1999 | Karmaker et al. | |
| 5,962,550 A | 10/1999 | Akahane et al. | |
| 6,250,193 B1 | 6/2001 | Head | |

* cited by examiner

*Primary Examiner*—Tae H Yoon
(74) *Attorney, Agent, or Firm*—Christensen O'Connor Johnson Kindness PLLC

(57) ABSTRACT

The present invention provides methods of constructing, reinforcing or modifying dental structures. The methods of the present invention include contacting a dental structure with dental resin and a triaxial material. In another aspect, the present invention provides dental structures including a triaxial material.

24 Claims, 1 Drawing Sheet

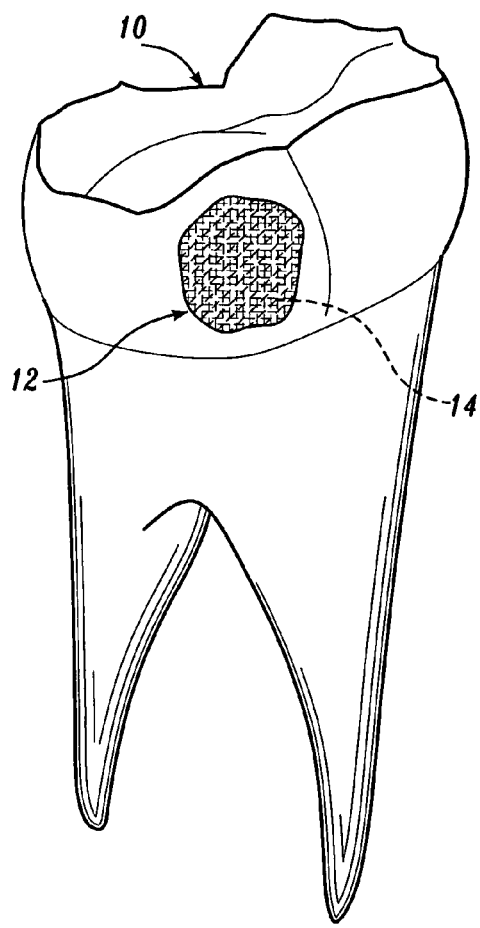
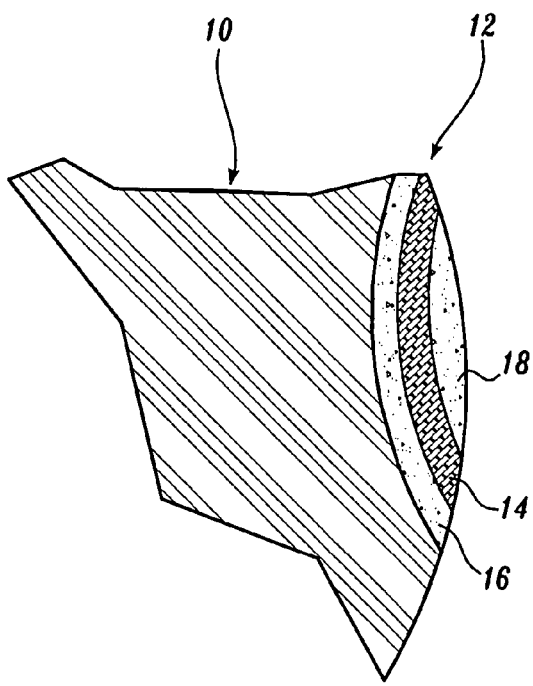
Fig. 1.
Fig. 2.
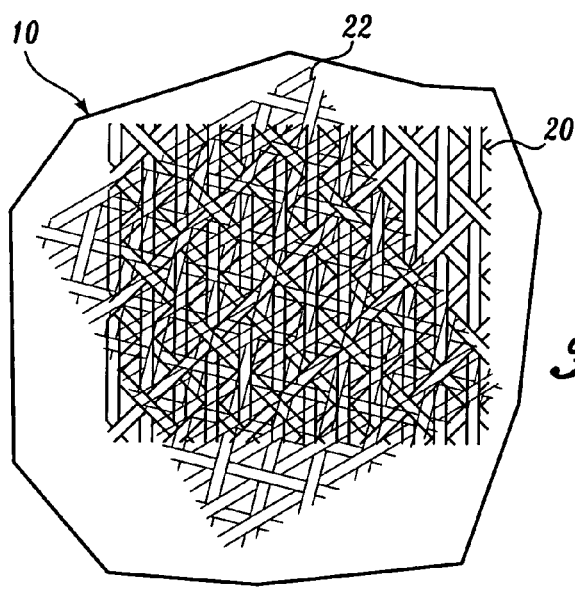
Fig. 3.

TRIAXIAL WEAVE FOR REINFORCING DENTAL RESINS

CROSS-REFERENCES TO RELATED APPLICATIONS

This application is a continuation of U.S. application Ser. No. 09/807,560 filed Apr. 12, 2001, now abandoned which is the National Stage of International Application No. PCT/US99/23563, filed Oct. 8, 1999, which claims the benefit of U.S. Provisional Application No. 60/104,265, filed Oct. 14, 1998.

FIELD OF THE INVENTION

This invention relates generally to methods for constructing, reinforcing or modifying dental restorations, dental appliances and prostheses (herein collectively referred to as "dental structures"), to dental reinforcing materials, and to reinforced dental structures. The invention also relates to the field of reinforced plastics and resins.

BACKGROUND OF THE INVENTION

Dental resins are polymeric materials that are used to construct dental structures such as restorations, prostheses and appliances. They are brittle, isomeric materials that exhibit relatively poor stress-bearing properties. In order to enhance the stress-bearing properties of dental resins and to minimize crack propagation, fiber reinforcements have been incorporated within dental resins. Fiber-reinforced dental resins are anisotropic materials that derive their strength and stiffness from reinforcing fibers embedded within the resin. The orientation of the reinforcing fibers provides directionality to the properties and performance attributes of the resin. The properties and performance attributes of fiber-reinforced dental resins include, for example, the ability of the resin to resist an externally applied shearing force.

Resins that include reinforcing fibers that are all oriented in one direction are restricted to performance in the direction of the reinforcing fibers. Thus, for example, the ability of a resin, that includes reinforcing fibers that are all oriented in one direction, to resist a shearing force applied at any angle other than along the axis of the reinforcing fibers approaches that of the unreinforced resin. Additionally, prior to curing, the resin is unstable since it can easily shear and thereby deform in a direction that is transverse to the direction of the fibers. Thus, for example, when an uncured resin, that includes reinforcing fibers that are all oriented in one direction, is being manipulated to conform to the contours of the teeth and or the dental arch, the material has a tendency to shear and deform in a direction that is transverse to the longitudinal axis of the fibers.

One attempted solution to the problem of shear and deformation of resins, that includes reinforcing fibers that are all oriented in one direction, has been to reinforce resins with biaxial weaves which are fabrics that include reinforcing fibers oriented in two, usually orthogonal, directions. Thus, biaxial weaves are able to resist shearing in two directions. Nonetheless, in a biaxial weave individual fiber bundles or yarns can still slide past each other, thereby causing the fabric to shear and deform. Further, biaxial weaves cannot resist deformation caused by an external force applied in any direction other than the two directions in which the reinforcing fibers are oriented. Deformation and shear is a problem, for example, when the fabric is impregnated with resin to form a composite, or when the fabric is manipulated to conform to the contours of a tooth or the dental arch.

Thus, there is a need for a method of constructing, reinforcing or modifying dental structures so that they are mechanically stable and can resist external forces applied from various directions.

SUMMARY OF THE INVENTION

The present invention provides methods for constructing, reinforcing or modifying dental structures. The methods of the present invention include the step of contacting a dental structure with resin and a triaxial material. Preferably the triaxial material is in the form of a triaxial braided or woven fabric. The resin can be any dental resin but is preferably selected from the group consisting of acrylic resin, urethane resin and methyl-methacrylate resin. The resin is most preferably bis-GMA resin. The triaxial material is preferably made from fibers selected from the group consisting of silk, nylon, polyester, polypropylene, aramid, ultra high molecular weight polyethylene, glass, boron, carbon and silicon carbide. The presently preferred aramid is Kevlar™, and the presently preferred, ultra high molecular weight polyethylene is Spectra™ which is preferably treated with gas plasma, more preferably with cold gas plasma. Representative examples of dental structures that can be treated in accordance with the methods of the present invention include, but are not limited to, the group consisting of fillings, periodontal splints, directly bonded endodontic posts, directly bonded endodontic cores, bonded orthodontic retainers, bridges (including directly bonded bridges), over-denture structures, composite-resin restorations, and implant retained maxial facial prostheses. The triaxial material preferably includes fibers oriented in three different directions, one of which directions is the direction of the long axis of the dental structure. More preferably from about 33.3% to about 50% of the fibers are oriented in the direction of the long axis of the dental structure.

In one presently preferred embodiment, the methods of the present invention include the steps of applying at least one layer of triaxial material to a resin portion of a dental structure; infusing the triaxial material with resin, and covering at least a portion of said triaxial material (preferably all of the triaxial material) with resin. In another presently preferred embodiment, the methods of the present invention utilize successive layers of triaxial material, each of the successive layers being offset by a desired angle with respect to a preceding layer.

In another aspect, the present invention provides dental structures including a triaxial material. Preferably the triaxial material is triaxial braided fabric and/or triaxial woven fabric. The triaxial material is preferably made from fibers selected from the group consisting of silk, nylon, polyester, polypropylene, aramid, ultra high molecular weight polyethylene, glass, boron, carbon and silicon carbide. The presently preferred aramid is Kevlar™, and the presently preferred, ultra high molecular weight polyethylene is Spectra™ which is preferably gas plasma-treated Spectra™, more preferably cold gas plasma-treated Spectra™. Representative examples of dental structures, including a triaxial material, of the present invention include, but are not limited to, the group consisting of fillings, periodontal splints, directly bonded endodontic posts, directly bonded endodontic cores, bonded orthodontic retainers, bridges (including directly bonded bridges), over-denture structures, composite-resin restorations, and implant retained maxial facial prostheses. The dental structures of the present invention preferably also include at least one type of dental resin that covers at least a portion of (preferably all of) the triaxial material. Presently preferred dental resins are selected from the group consisting of acrylic resin, urethane resin and methyl-methacrylate resin. The presently most preferred resin is bis-GMA resin. The triaxial material preferably has a refractive index similar to, preferably identical to, that of the dental resin.

The triaxial material preferably includes fibers oriented in three different directions, wherein one of the directions is the direction of the long axis of the dental structure. More preferably, from about 33.3% to about 50% of the fibers are oriented in the direction of said long axis. In a presently preferred embodiment, the present invention provides dental structures including more than one, successive layer of triaxial material, each of the successive layers being offset by a desired angle with respect to a preceding layer.

In another embodiment of the present invention, a stress-bearing beam framework, such as a dental bridge, is constructed from multiple layers of triaxial material and resin.

BRIEF DESCRIPTION OF THE DRAWINGS

FIG. 1 shows a dental structure including a filling that includes a portion of triaxial material.

FIG. 2 shows a cross section of a dental structure and a filling.

FIG. 3 shows a dental structure including a first layer of triaxial material superimposed upon a second layer of triaxial material, wherein the first triaxial material layer is offset with respect to the second triaxial material layer.

DETAILED DESCRIPTION OF THE PREFERRED EMBODIMENT

As used herein, the term "triaxial material" means a material having three sets of fibers oriented in three different directions. Preferably, the triaxial materials useful in the practice of the present invention are in the form of a braided ribbon or woven fabric.

As used herein, the term "resin" encompasses pure resins (such as acrylic resins, urethane and bis-GMA resin) and dental, particulate, composite resins (including macrofils, microfils and hybrids).

As used herein, the term "dental structure" refers to natural structures, such as teeth, and synthetic structures, such as a dental bridge, that constitute, or are applied to, the dentition of an animal. Thus, for example, natural teeth, dental restorations, dental prostheses and dental appliances are all encompassed by the term "dental structure."

The present invention provides methods for constructing, reinforcing or modifying dental structures. The methods of the present invention include the step of contacting a dental structure with resin and a triaxial material. Preferably the triaxial material is in the form of a triaxial weave or fabric. In one embodiment of the methods of the present invention, one or more layers of a triaxial material is applied to a resin portion of a dental structure, the triaxial material is infused with a resin, and at least a portion of the triaxial material, preferably all of the triaxial material, is covered with more resin.

In another aspect, the present invention provides dental structures (such as a tooth) constructed, reinforced or modified with a triaxial material. FIG. 1 shows a dental structure 10 including a filling 12 that includes a portion of triaxial material 14. In the example shown in FIG. 1, dental structure 10 is a tooth. FIG. 2 shows a cross section of dental structure 10 and filling 12. Filling 12 includes a layer of triaxial material 14 between a first dental resin layer 16 and a second dental resin layer 18. First dental resin layer 16 mainly serves to bond filling 12 to dental structure 10.

The triaxial materials utilized in the practice of the present invention include three sets of intersecting fibers which are oriented, along their longitudinal axes, in three, different directions and which intersect at predetermined angles. The orientation of the three sets of fibers, and the angles of intersection between intersecting fibers, largely governs the ability of the triaxial material to resist deformation by one or more externally-applied forces. The three sets of fibers can each include more than one type of fiber mixed in various proportions depending on the desired properties of the triaxial material. Additionally, the proportion of fibers disposed in each of the three directions can be varied. Preferably the triaxial materials useful in the practice of the present invention will have from about 33.3% to about 50% of the total number of fibers disposed in the axial direction.

By way of non-limiting example, the fibers of the triaxial material can be natural fibers, such as silk; synthetic, organic fibers, such as nylon, polyester, polypropylene, aramids (such as Kevlar™), ultra high molecular weight polyethylene (such as Spectra™); and synthetic, inorganic fibers, such as glass, boron, carbon and silicon carbide. The presently preferred material from which the fibers of the triaxial material are synthesized is Spectra™. Kevlar™ is commercially available from DuPont, Wilmington, Del. Spectra™ is commercially available from Allied Signal, Petersburg, Va.

Triaxial materials useful in the practice of the present invention can be manufactured utilizing standard techniques well known to one of ordinary skill in the art. Prior to use, triaxial materials useful in the practice of the present invention can be cut from a bolt of cloth or preferably from a ribbon. By ribbon is meant a long and narrow piece of fabric. Preferably the triaxial material will be cut to a width of from about 1 millimeter (mm) to about 4 mm, and will have a thickness of about 0.2 mm. Preferably the triaxial material will have a denier value of from about 100 to about 215. The triaxial material can be used as is, or it may be provided and used in a form that is already impregnated with resin. The triaxial material may also be treated to promote adhesion with the resin. For example, a presently preferred material from which the triaxial material can be constructed is Spectra™ which is a high-strength, extended chain polyethylene. It is known that gas plasma treatment of Spectra™ fiber can result in epoxy composites which possess outstanding properties. Preferably, cold gas plasma is utilized to treat Spectra™ fiber. In general, the technique of gas plasma treatment involves placing triaxial material within a reaction chamber, introducing process gas into the reaction chamber, and subjecting the process gas to a high energy discharge (such as an ultraviolet glow discharge) to generate process gas ions which abstract surface hydrogen atoms from the triaxial material and replace them with polar groups. The primary objective of this gas plasma treatment is surface modification, wherein hydrogen atoms are abstracted and replaced with polar groups (e.g., hydroxyl, carboxyl and the like). The presence of polar or functional chemical groups on the surface of the fiber enhances wettability by and reactivity with a resin matrix, thus promoting excellent adhesion between the fiber and the resin. Individual fibers can be plasma-treated, but preferably triaxial material is subjected to plasma treatment.

Single as well as multiple layers of triaxial material are contemplated in connection with the present invention.

When multiple layers of triaxial material are utilized, they may be exactly superimposed on each other, or each successive layer may be offset by a desired angle with respect to the preceding layer. A benefit of utilizing multiple, offset layers of triaxial material in a dental structure is that the completed dental structure can better resist shear forces applied from any angle. For example, FIG. 3 shows a dental structure 10 including a first layer of triaxial material 20 superimposed upon a second layer of triaxial material 22, first triaxial material layer 20 being offset with respect to second triaxial material layer 22.

Preferably, triaxial materials useful in the practice of the present invention are translucent and have a refractive index that is similar, preferably identical, to that of the dental resin with which the triaxial material is impregnated in a dental structure.

Typically, the triaxial material incorporated into a dental structure will be covered with resin. While the resinous covering will generally be the same resin as the underlying resin layer, a different resinous covering could also be employed, as long as it exhibits sufficient adhesion both to the triaxial material and to the underlying resin.

To prepare the triaxial material for use, a portion of the triaxial material is cut to the desired size and shape. The triaxial material is preferably wetted with a low viscosity resin before it is impregnated with a more viscous resin. For example, before using an acrylic resin, the triaxial material is preferably wetted with the acrylic resin monomer, which serves as the thinning agent.

The amount of triaxial material used to reinforce a particular dental structure will depend upon the size and shape of the area to be reinforced and the direction of the forces exerted upon the structure. Based on the conventional understanding and experience of those working in the field of dentistry it will typically be possible to predict in advance which portions of a given dental structure will need reinforcement.

In general, the greater the fiber volume proportion of triaxial material used to reinforce the dental structure, the greater will be the strength of the reinforced structure. Thus, one of ordinary skill in the art will be able to tailor the strength of a given dental structure by adding more or less of the triaxial material to the resinous portion of the structure.

All resinous dental structures can be constructed, reinforced or modified in accordance with the methods of the present invention. Specific examples of dental structures that can be constructed, reinforced or otherwise altered in accordance with the methods of the present invention include, but are not limited to: fillings, periodontal splints; directly bonded endodontic posts and cores; bonded orthodontic retainers; directly bonded bridges; immediate replacement of avulsed or extracted teeth; reinforcing long-term provisional bridges; denture and bridge repair; reinforcing overdenture components; reinforcing composite-resin restorations; reinforcing implant retained maxial facial prostheses.

Several layers of triaxial material can be utilized to construct a dental structure. For example, it is preferable to utilize several layers of triaxial material in the construction of a stress-bearing, beam framework such as a dental bridge. Some dental structures, such as a filling or a dental splint holding two teeth together, will preferably incorporate only a single layer of triaxial material. As is well known to one of ordinary skill in the art, some dental structures, such as a dental bridge, can be constructed either directly on the teeth or outside of the mouth and then applied to the teeth.

All resins used in dentistry can be utilized in the practice of the present invention. The basic requirements of the resin useful in the practice of the present invention are that it be compatible with a particular dental use and capable of sufficiently adhering to the triaxial material to result in a suitable reinforced dental structure. Generally, the resin will be a synthetic resin. Preferably the resin is an acrylic resin, such as bis-GMA resin, which is a standard resin familiar to dentists. The presently preferred resins are bis-GMA, methyl-methacrylate and urethane resins. Bis-GMA resins are commercially available from, for example, BISCO Dental Products, Itaska, Ill., and DENTSPLY CAULK, Milford, Conn.

The following examples merely illustrate the best mode now contemplated for practicing the invention, but should not be construed to limit the invention.

EXAMPLE 1

Constructing a Splint Directly on the Teeth

The methods of the present invention can be used to construct a splint directly on teeth as described herein. A piece of triaxial material is cut to the desired dimensions. The teeth that are to be splinted are prepared in a standard manner by cleaning with pumice, acid-etching and applying unfilled bonding resin. If desired, a groove may be cut in the surface of the teeth. A layer of filled, composite resin is then applied to the prepared teeth.

The cut, triaxial material is wetted with unfilled bonding resin. The excess, unfilled bonding resin is blotted with lint-free gauze, and the triaxial material is applied to the composite on the teeth. The triaxial material is then conformed to the shape of the teeth to which it is applied, and excess resin is removed. The resin is then polymerized, for example by exposure to light. An additional layer of resin is applied over the triaxial material. Either a filled composite, or a moderately filled composite can be used. The resin is then polymerized and polished.

While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A method of constructing, reinforcing or modifying a dental bridge comprising contacting said dental bridge with dental resin and a multiplicity of layers of triaxial material, each layer of triaxial material having first, second, and third fiber sets, the first fiber set extending along its longitudinal axis in a direction different than a direction the longitudinal axis of the second fiber set and the third fiber set extend, the second fiber set extending along its longitudinal axis in a direction different than a direction the longitudinal axis of the third fiber set extends.

2. The method of claim 1 wherein said resin is selected from the group consisting of acrylic resin, urethane resin and methyl-methacrylate resin.

3. The method of claim 1 wherein said resin is Bisphenol-A-glycidyldimethacrylate.

4. The method of claim 1 wherein said triaxial material is selected from the group consisting of triaxial braided fabric and triaxial woven fabric.

5. The method of claim 1 wherein said triaxial material comprises fibers selected from the group consisting of silk, nylon, polyester, polypropylene, aramid, ultra high molecular weight polyethylene, glass, boron, carbon and silicon carbide.

6. The method of claim 1 wherein said triaxial material comprises aramid fibers.

7. The method of claim 1 wherein said triaxial material comprises ultra high molecular weight polyethylene fibers.

8. The method of claim 7 wherein said ultra high molecular weight polyethylene fibers are treated with gas plasma.

9. The method of claim 8 wherein said ultra high molecular weight polyethylene fibers are treated with cold gas plasma.

10. The method of claim 1 further comprising the steps of:
    (a) applying at least two layers of said triaxial material to a resin portion of a dental bridge;
    (b) infusing said triaxial material with resin; and
    (c) covering at least a portion of said triaxial material with resin.

11. The method of claim 1 wherein more than one, successive layer of said triaxial material are utilized, each of said successive layers being offset by a desired angle with respect to a preceding layer of triaxial material.

12. A structure comprising a dental bridge comprising a multiplicity of layers of a triaxial material, each layer of triaxial material having first, second, and third fiber sets, the first fiber set extending along its longitudinal axis in a direction different than a direction the longitudinal axis of the second fiber set the third fiber set extend, the second fiber set extending along its longitudinal axis in a direction different than a direction the longitudinal axis of the third fiber set extends.

13. The structure of claim 12 wherein said triaxial material is selected from the group consisting of triaxial braided fabric and triaxial woven fabric.

14. The structure of claim 12 wherein said triaxial material comprises fibers selected from the group consisting of silk, nylon, polyester, polypropylene, aramid, ultra high molecular weight polyethylene, glass, boron, carbon and silicon carbide.

15. The structure of claim 12 wherein said triaxial material comprises aramid fibers.

16. The structure of claim 12 wherein said triaxial material comprises ultra high molecular weight polyethylene fibers.

17. The structure of claim 16 wherein said ultra high molecular weight polyethylene fibers are gas plasma-treated ultra high molecular weight polyethylene fibers.

18. The structure of claim 17 wherein said ultra high molecular weight polyethylene fibers are cold gas plasma-treated ultra high molecular weight polyethylene fibers.

19. The structure of claim 12 further comprising dental resin.

20. The structure of claim 19 wherein said dental resin is selected from the group consisting of acrylic resin, urethane resin and methyl-methacrylate resin.

21. The structure of claim 19 wherein said dental resin is Bisphenol-A-glycidyldimethacrylate.

22. The structure of claim 19 wherein said triaxial material is covered with dental resin.

23. The structure of claim 12 further comprising more than one, successive layer of said triaxial material, each of said successive layers being offset by a desired angle with respect to a preceding layer.

24. The structure of claim 19 wherein said triaxial material has a refractive index similar to that of said dental resin.

* * * * *

UNITED STATES PATENT AND TRADEMARK OFFICE
CERTIFICATE OF CORRECTION

PATENT NO.       : 7,186,760 B2                                          Page 1 of 1
APPLICATION NO. : 10/656088
DATED            : March 6, 2007
INVENTOR(S)      : D.N. Rudo It is certified that error appears in the above-identified patent and that said Letters Patent is hereby corrected as shown below:

Title Page, Item (63) Related U.S. Appln. Data "Continuation of application No. 09/807,560, filed as application No. PCT/US99/23563 on Oct. 8, 1999, now abandoned." should read
--Continuation of application No. 09/807,560, filed on Apr. 12, 2001, now abandoned, which is a 371 of application No. PCT/US99/23563, filed on Oct. 8, 1999.--

Column 7, line 28 (Claim 12, line 6) "second fiber set third fiber set" should read
--second fiber set and third fiber set--

Signed and Sealed this

Eighteenth Day of September, 2007

JON W. DUDAS
*Director of the United States Patent and Trademark Office*